US008353468B2

(12) United States Patent
Cuzydlo

(10) Patent No.: US 8,353,468 B2
(45) Date of Patent: Jan. 15, 2013

(54) DEVICE FOR CONTROLLING THE FLOW OF ANESTHETIC FROM A RESERVOIR

(75) Inventor: Michael Cuzydlo, Orchard Park, NY (US)

(73) Assignee: Piramal Critical Care, Inc., Orchard Park, NY (US)

( * ) Notice: Subject to any disclaimer, the term of this patent is extended or adjusted under 35 U.S.C. 154(b) by 696 days.

(21) Appl. No.: 12/274,819

(22) Filed: Nov. 20, 2008

(65) Prior Publication Data

US 2010/0108184 A1 May 6, 2010

Related U.S. Application Data

(60) Provisional application No. 61/110,401, filed on Oct. 31, 2008, provisional application No. 61/110,417, filed on Oct. 31, 2008.

(51) Int. Cl.
*A01G 25/14* (2006.01)
(52) U.S. Cl. .......................................... 239/378; 239/337
(58) Field of Classification Search .................. 239/302, 239/303, 378, 390, 443, 569, 581.1, 581.2, 239/337; 141/351
See application file for complete search history.

(56) References Cited

U.S. PATENT DOCUMENTS

| 2,584,167 | A |   | 2/1952  | Sundholm |
|-----------|---|---|---------|----------|
| 2,597,775 | A | * | 5/1952  | Brown ........................... 239/476 |
| 2,989,091 | A |   | 6/1961  | Lowenthal |
| 3,216,630 | A |   | 11/1965 | Stull |
| RE26,193  | E |   | 4/1967  | Labat |
| 3,326,402 | A |   | 6/1967  | Randazzo |
| 3,720,352 | A | * | 3/1973  | Kozlowski ..................... 222/132 |
| 3,744,526 | A |   | 7/1973  | MacNiel |
| 4,421,297 | A |   | 12/1983 | Pongrass et al. |
| 4,509,554 | A |   | 4/1985  | Failla |
| 4,949,875 | A |   | 8/1990  | Kuo |
| 5,026,924 | A |   | 6/1991  | Cicco |
| 5,287,898 | A |   | 2/1994  | Falb et al. |
| 5,381,836 | A |   | 1/1995  | Braatz et al. |
| 5,427,145 | A |   | 6/1995  | Grabenkort |

(Continued)

FOREIGN PATENT DOCUMENTS

RU        2329832        7/2008

(Continued)

OTHER PUBLICATIONS

International Search Report corresponding to International Application No. PCT/US2009/051397 dated Sep. 15, 2009.

(Continued)

*Primary Examiner* — Davis Hwu
(74) *Attorney, Agent, or Firm* — Marc S. Kaufman; Reed Smith LLP

(57) ABSTRACT

The present invention may be embodied as a device for selectively opening or closing an anesthetic reservoir, the device having a first component adaptable to a reservoir and a second component adaptable to a vaporizer. The first component may have a base, a nozzle, and a through-hole. The second component may have a support member with a knob for engaging the through-hole of the first component and preventing liquid from flowing from the through-hole. The first and second components may be threaded to engage with each other such that when the components are twisted relative to each other, the knob may move toward or away from the through-hole to prevent or allow liquid flow.

10 Claims, 10 Drawing Sheets

U.S. PATENT DOCUMENTS

| | | | |
|---|---|---|---|
| 5,488,973 | A | 2/1996 | Yamamuro |
| 5,505,236 | A | 4/1996 | Grabenkort et al. |
| 5,609,276 | A | 3/1997 | Greatbatch |
| 5,617,906 | A | 4/1997 | Braatz et al. |
| 5,682,874 | A | 11/1997 | Grabenkort et al. |
| 5,687,777 | A | 11/1997 | Dobson et al. |
| 5,915,427 | A | 6/1999 | Grabenkort |
| 6,135,329 | A | 10/2000 | Stoneberg et al. |
| 6,286,505 | B1 | 9/2001 | Psaros |
| 6,296,623 | B2 | 10/2001 | Spinello |
| 6,582,415 | B1 | 6/2003 | Fowles et al. |
| 6,585,016 | B1 | 7/2003 | Falligant et al. |
| 6,758,376 | B1 | 7/2004 | Clodfelter et al. |
| 6,800,786 | B1 | 10/2004 | Rozov et al. |
| 6,817,390 | B2 | 11/2004 | Falligant |
| 7,159,616 | B2 | 1/2007 | Watson et al. |
| 7,546,856 | B2 | 6/2009 | Chotenovsky |
| 2006/0130930 | A1 | 6/2006 | Turker et al. |
| 2007/0066955 | A1 | 3/2007 | Sparholt et al. |
| 2007/0131725 | A1 | 6/2007 | Friedman |
| 2007/0199616 | A1 | 8/2007 | Chotenovsky |
| 2007/0204931 | A1 | 9/2007 | Freed et al. |
| 2007/0204932 | A1 | 9/2007 | Freed et al. |
| 2008/0302836 | A1 | 12/2008 | Mathis |
| 2009/0260627 | A1 | 10/2009 | Cuzydlo et al. |
| 2010/0018528 | A1 | 1/2010 | Cuzydlo |
| 2010/0018607 | A1 | 1/2010 | Cuzydlo |
| 2010/0199987 | A1 | 8/2010 | Cuzyldo |
| 2010/0199988 | A1 | 8/2010 | Cuzyldo et al. |
| 2010/0199989 | A1 | 8/2010 | Cuzyldo et al. |
| 2010/0199990 | A1 | 8/2010 | Cuzyldo |
| 2010/0224285 | A1 | 9/2010 | Cuzydlo |
| 2010/0319690 | A1 | 12/2010 | Cuzydlo |

FOREIGN PATENT DOCUMENTS

| | | |
|---|---|---|
| SU | 1678380 | 9/1991 |

OTHER PUBLICATIONS

International Search Report corresponding to International Application No. PCT/US2009/051391 dated Sep. 17, 2009.
International Search Report corresponding to International Application No. PCT/US2009/62465 dated Jan. 14, 2010.
International Search Report corresponding to International Application No. PCT/US2009/62461 dated Feb. 12, 2010.
International Search Report corresponding to International Application No. PCT/US2009/066535 dated Mar. 12, 2010.
International Search Report corresponding to International Application No. PCT/US2010/026317 dated May 19, 2010.
International Search Report corresponding to International Application No. PCT/US2010/038179 dated Aug. 11, 2010.
International Preliminary Report on Patentability corresponding to International Application No. PCT/US2009/051391 dated Feb. 3, 2011.
International Preliminary Report on Patentability corresponding to International Application No. PCT/US2009/051397 dated Feb. 3, 2011.
Search Report TR 10/066 established by Russian Patent Office corresponding to Turkish Application No. 2009/08207 dated Aug. 9, 2010.
Search Report TR 09/591 established by Russian Patent Office corresponding to Turkish Application No. 2009/07308 dated Jun. 10, 2010.
Search Report TR 10/041 established by Russian Patent Office corresponding to Turkish Application No. 2009/00676 dated Aug. 9, 2010.
Search Report TR 10/130 established by Russian Patent Office corresponding to Turkish Application No. 2009/09123 dated Sep. 14, 2010.
Examination Report TR 08/349 corresponding to Turkish Application No. 2007/03378 dated Jan. 19, 2009.
Examination Report TR 09/551 corresponding to Turkish Application No. 2007/03378 dated May 10, 2010.
Office Action Dated Jun. 22, 2012 in U.S. Appl. No. 12/496,895, Confirmation No. 5380.
Office Action Dated Mar. 7, 2012 in U.S. Appl. No. 12/274,819, Confirmation No. 1977.
Office Action Dated Sep. 26, 2011 in U.S. Appl. No. 12/274,819, Confirmation No. 1977.
International Search Report corresponding to International Application No. PCT/US09/62460.
Office Action Dated Apr. 27, 2012 in U.S. Appl. No. 12/608,081, Confirmation No. 5812.
Office Action Dated May 16, 2012 in U.S. Appl. No. 12/608,092, Confirmation No. 5825.
Office Action Dated May 23, 2012 in U.S. Appl. No. 12/630,174, Confirmation No. 9260.
Office Action Dated May 23, 2012 in U.S. Appl. No. 12/631,936, Confirmation No. 2889.
International Search Report corresponding to International Application No. PCT/US09/66920.
Office Action Dated Oct. 11, 2012 U.S. Appl. No. 12/608,092, Confirmation No. 5825.

* cited by examiner

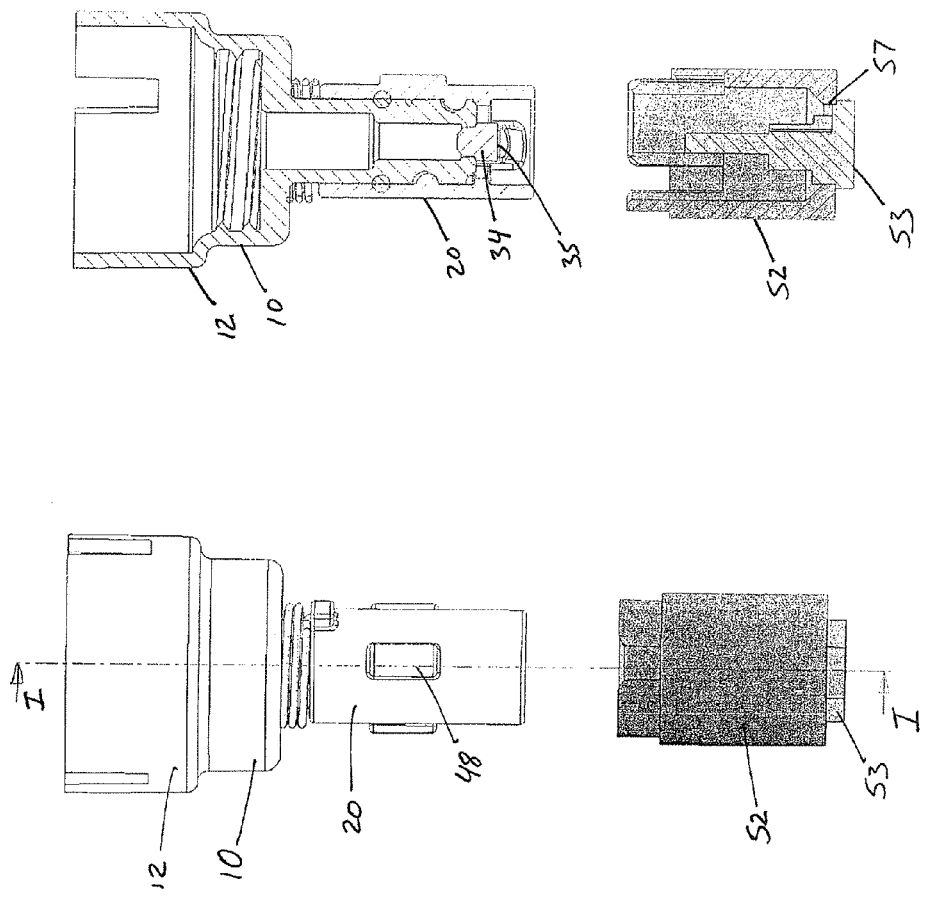

DEVICE FOR CONTROLLING THE FLOW OF ANESTHETIC FROM A RESERVOIR

CROSS-REFERENCE TO RELATED APPLICATION

This application claims the benefit of priority to U.S. provisional patent application Ser. No. 61/110,401, filed on Oct. 31, 2008, now pending and U.S. provisional patent application Ser. No. 61/110,417, filed on Oct. 31, 2008, now pending.

FIELD OF THE INVENTION

The present invention relates to valves for controlling liquid anesthetic flow from a container.

BACKGROUND OF THE INVENTION

Liquid anesthetics are often packaged in glass bottles and shipped to a location where they may be used to anesthetize a patient, who is undergoing a medical or dental procedure. Such anesthetics may also be used to induce analgesia in a patient who is undergoing a medical or dental procedure. In order to administer the anesthetic, the contents of the glass bottle are placed in a vaporizer. The vaporizer may be used to vaporize the anesthetic, and provide the vaporized anesthetic in a desired amount to the patient.

Inhalable anesthetics are typically volatile substances with relatively low boiling points and high vapor pressure. Preferably, the anesthetic should be used in a way which will ensure there is little or no release to the atmosphere at all stages of handing. In order to transfer the liquid anesthetic to the vaporizer, the bottle must be opened. Since it is unwise to expose medical personnel performing the procedure to the anesthetic, and since anesthetics are expensive, devices have been developed to minimize the release of anesthetic from the bottle to the environment surrounding the vaporizer.

BRIEF SUMMARY OF THE INVENTION

The present invention may be embodied as a device for controlling the flow of liquid anesthetic from an anesthetic reservoir. Such a device may include a first component capable of being sealed and affixed to a reservoir and a second component adaptable to a vaporizer. The first component may have a base and a nozzle, the nozzle being externally threaded. A through-hole may extend through the base and nozzle. The second component may be cylindrically shaped and may have an inner surface which defines an aperture. A support member may extend into the aperture and a knob may extend from the support member for engaging the through-hole of the first component and preventing liquid and vapor from flowing via the through-hole. A portion of the second component may be internally threaded. The threads of the first and second components may be configured to engage with each other such that when the components are twisted relative to each other, the knob may move toward or away from the through-hole to prevent or allow liquid flow.

A torsion spring may be attached to the first component and the second component to bias the components to prevent fluid flow from the assembly. In this manner, anesthetic in the reservoir can not escape unless a force is applied to counter the force imposed by the torsion spring. The second component may have a stud with a mounting hole for attachment of the torsion spring. An O-ring may be disposed on the first component to provide a fluid seal between the first component and the second component.

The second component may have a cylindrical outer surface which may further comprise one or more indexing tabs. The indexing tabs may be evenly or unevenly spaced around a circumference of the second component. The indexing tabs may be configured for engaging one or more keyways in the vaporizer. The keyway(s) may be configured such that only a second component with a specific indexing tab arrangement may be inserted into the vaporizer.

The support member may have a downstream side suitable for depressing a plunger located on a vaporizer receiving port in order to open the vaporizer for additional anesthetic.

The base of the first component may be internally threaded for engaging threads located on the reservoir. The first component may have at least two notches for receiving indexing nubs on the reservoir such that when the configuration of the notches coincides with the that of the indexing nubs, the proper base will be used with the reservoir.

DESCRIPTION OF THE DRAWINGS

For a fuller understanding of the nature and objects of the invention, reference should be made to the following detailed description taken in conjunction with the accompanying drawings, in which:

FIG. 10A depicts a device according to another embodiment of the invention and a vaporizer receiving port—both in "closed" positions;

FIG. 10B is a cross-sectional view of the device and vaporizer receiving port of FIG. 10A taken along I-I in FIG. 10A;

DETAILED DESCRIPTION OF THE INVENTION

Figure 9B:
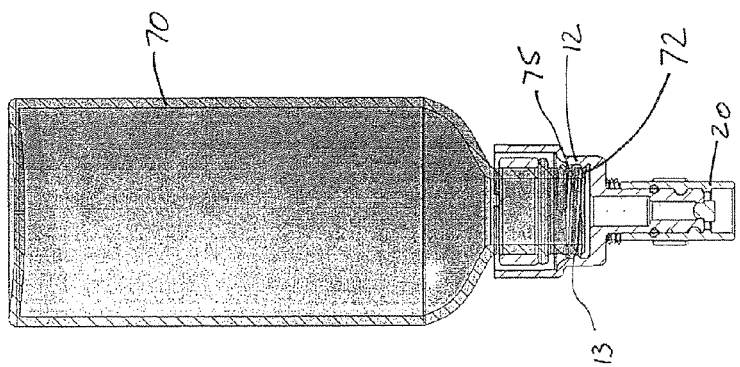
FIG. 9B is a cross-sectional view of the device and reservoir of FIG. 9A taken along H-H in FIG. 9A.
Figure 9A:
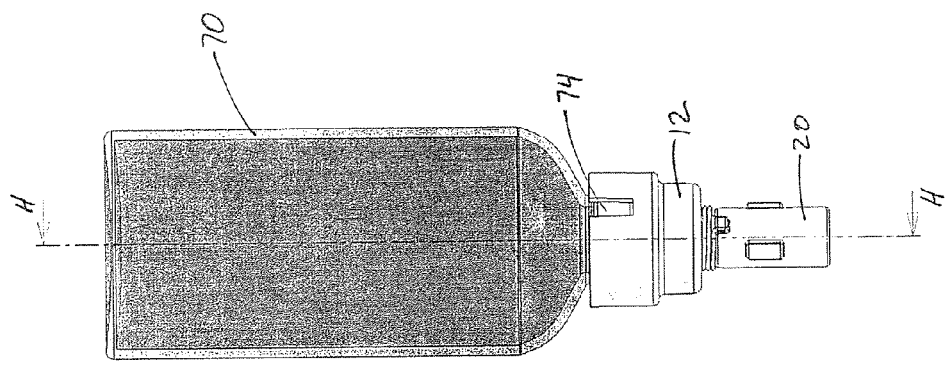
FIG. 9A depicts the device of FIG. 1 attached to a reservoir.

The present invention may be embodied as a device 10 for selectively opening or closing an anesthetic reservoir 70. One such device 10, depicted in FIG. 1, may include a first component 12 and a second component 20. The first component 12 may have a base 14 and a nozzle 16. The first component 12 may be adaptable to a reservoir 70 so that the base 14 may be in a sealing relation with an opening 72 of the reservoir 70, for example as depicted in FIGS. 9A and 9B. The base 14 may be attached to the reservoir 70 using, for example, internal threads 13, which are capable of engaging external threads 75 located on the reservoir 70 or on a collar of the reservoir 70. The base 14 may include at least two notches 17 for engaging indexing nubs 74 on the reservoir 70 or on a collar of the reservoir 70. A particular configuration of the nubs 74 may be used with a particular anesthetic. When the base 14 has notches 17 that coincide with the nubs 74, the proper base 14 for that anesthetic will be used.

Figure 3A:
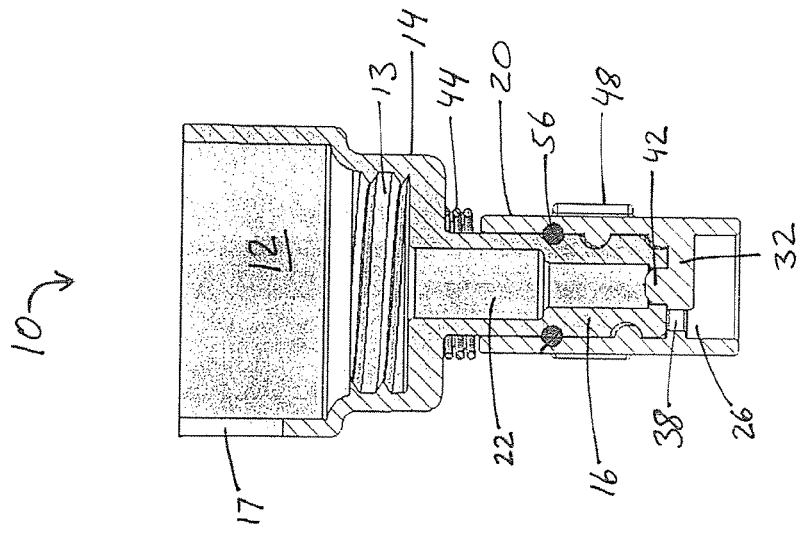
FIG. 3A is a cross-section of the device shown in FIG. 1 taken along A-A showing the device in an "open" position.
Figure 3B:
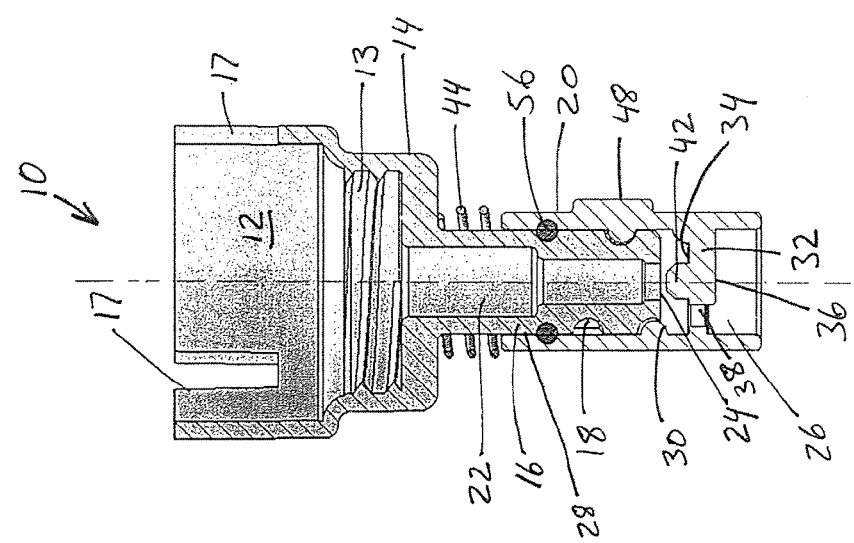
FIG. 3B depicts a cross-section (along B-B) of the device shown in FIG. 2 showing the device in the "closed" position.
Figure 4D:
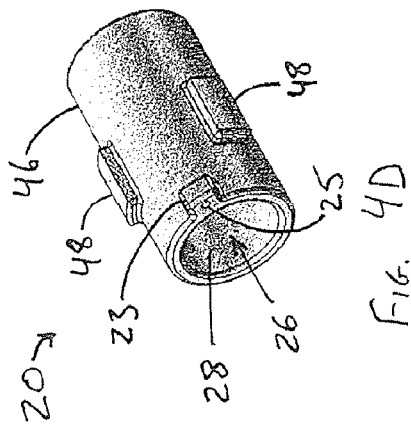
FIG. 4D is a perspective view of the second component shown in FIGS. 4A and 4C.
Figure 4C:
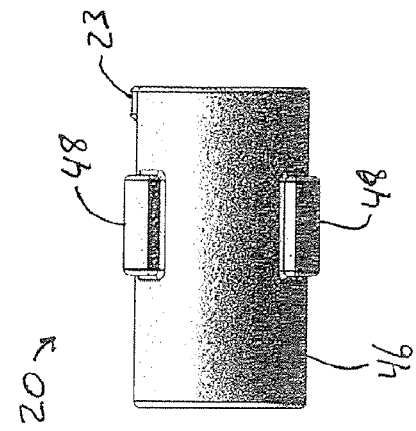
FIG. 4C is a side view of the second component shown in FIG. 4A.
Figure 4A:
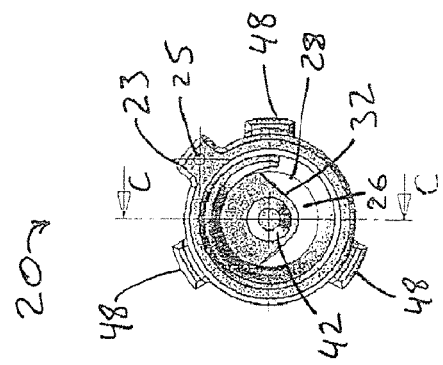
FIG. 4A depicts an embodiment of the second component of a device according to the invention as viewed along the aperture.
Figure 4B:
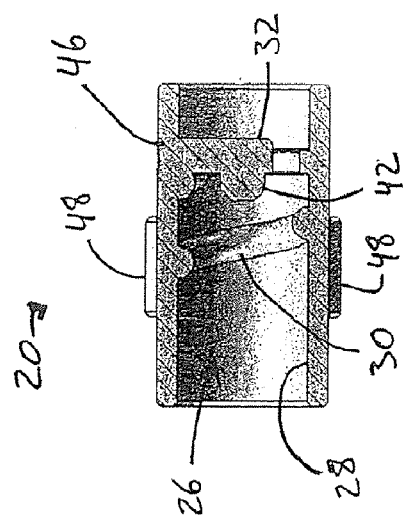
FIG. 4B is a cross-sectional view of the second component shown in FIG. 4A taken along C-C in FIG. 4A.
Figure 5D:
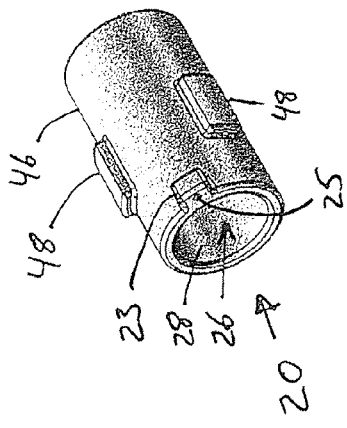
FIG. 5D is a perspective view of the second component shown in FIGS. 5A and 5C.
Figure 5C:
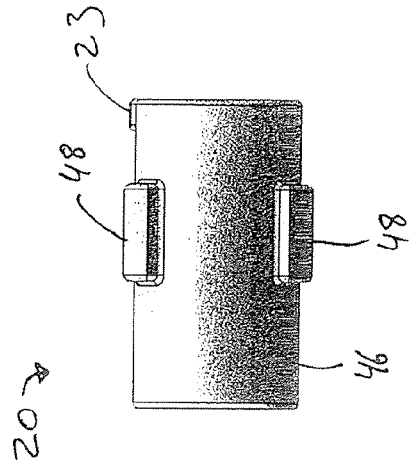
FIG. 5C is a side view of the second component shown in FIG. 5A.
Figure 5A:
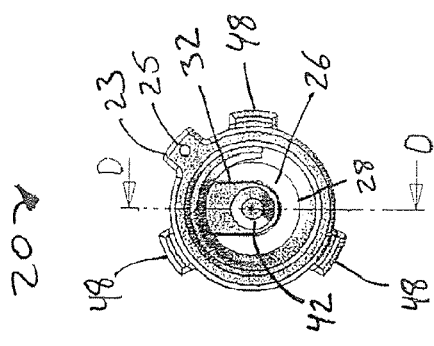
FIG. 5A depicts another embodiment of the second component of a device according to the invention as viewed along the aperture.
Figure 5B:
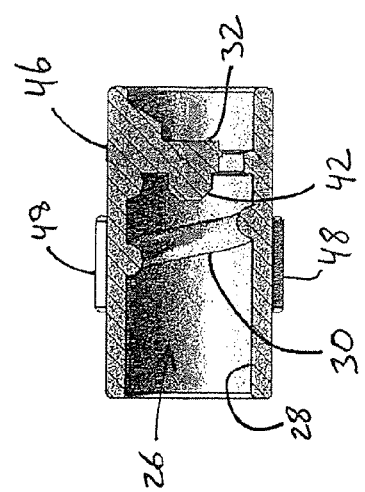
FIG. 5B is a cross-sectional view of the second component shown in FIG. 5A taken along D-D in FIG. 5A.

FIGS. 3A and 3B depict a device 10 wherein the nozzle 16 may have an externally threaded portion 18. A through-hole 22 may extend through the base 14 and the nozzle 16. In this manner, a liquid contained within the reservoir 70 may flow from the reservoir 70 through the through-hole 22 and exit an orifice 24 in the first component 12. Upon exiting the orifice 24, the liquid is provided to the second component 20.

The second component 20 may have an aperture 26 defined by an inner surface 28 (see, e.g., FIGS. 4A-4D and 5A-5D). The inner surface 28 may have an internally threaded portion 30 to receive the externally threaded portion 18 of the nozzle 16. A support member 32 may extend into the aperture 26 from the inner surface 28. The support member 32 may occlude a portion of the aperture 26 but does not divide the aperture 26. In this manner, there may be a single passageway 38 leading from a first side 34 of the support member 32 to a second side 36 of the support member 32 (see, e.g., FIGS. 3A and 3B).

Figure 1:
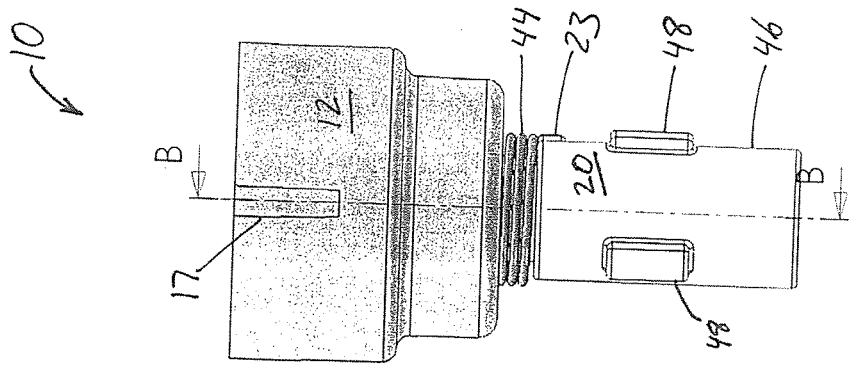
FIG. 1 depicts a device according to the invention connected to an anesthetic agent bottle.
Figure 2:
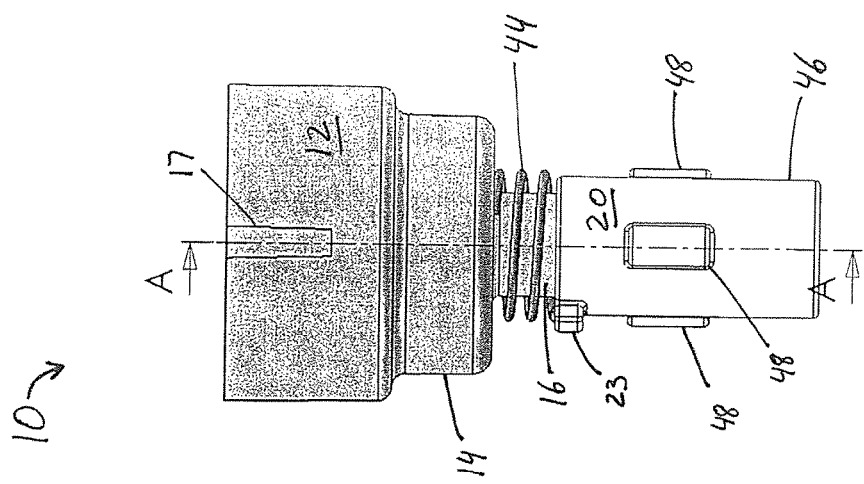
FIG. 2 depicts the device of FIG. 1 showing the device in a "closed" position.

A knob 42 may extend from support member 32 toward the internally threaded portion 30. In this manner, by twisting the first component 12 and second component 20 relative to each other, the externally and internally threaded portions 18, 30 cause the knob 42 to move toward or away from the orifice 24, depending on the direction in which twisting occurs. The knob 42 may be caused to be inserted in the orifice 24 and seated against the nozzle 16 thereby preventing liquid and vapor, which may be contained in the reservoir 70, from traveling from the reservoir 70 through the orifice 24 via the through-hole 22. This may result in the device configured in a "closed" position as depicted in FIGS. 2 and 3B. Twisting the components 12, 20 to move the knob 42 away from the orifice 24 may result in an "open" position as depicted in FIGS. 1 and 3A.

In operation, a single path is provided for liquid to travel from the reservoir 70, through the through-hole 22 of the first component 12, and through the aperture 26 of the second component 20. Similarly, vapor may travel in the opposite direction to the reservoir 70 along the same path. Because only a single path is provided, liquid will not travel from the reservoir 70 along this path at the same time that vapor is traveling into the reservoir 70, and vice versa.

A torsion spring 44 may be attached to the first component 12 and the second component 20 in order to provide a spring force to bias the first component 12 and the second component 20 to a pre-determined position relative to each other. The second component 20 may include a stud 23 having a mounting hole 25 for attaching the torsion spring 44 (see, e.g., FIGS. 4A and 4D). The torsion spring 44 may bias the device 10 to a "closed" position wherein the knob 42 is seated in the orifice 24 and against the nozzle 16 as described above. In this manner, anesthetic in the reservoir 70 cannot escape unless a force is applied to the first or second components 12, 20 to counter the force imposed by the torsion spring 44. For example, when a reservoir 70 with an attached device 10 is inserted into a vaporizer, twisting the reservoir 70 requires a force sufficient to overcome the force of the torsion spring 44 so that the first component 12 is caused to rotate and thereby open the device 10.

The threads 18, 30 between the first and second component 12, 20 may be configured such that rotating the reservoir 70 to open the device 10 will cause the threads 13, 75 between the reservoir 70 and the first component 12 to engage further ("tighten"). In this manner, there is a reduced risk of detaching a reservoir 70 full of anesthetic from the device 10 when trying to open the device 10. When rotating the reservoir 70 to close the device 10, the reservoir 70 is likely to be emptied of its contents, and therefore the risks associated with detachment are reduced.

Figure 6D:
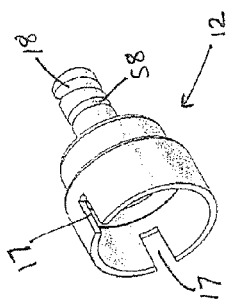
FIG. 6D is a perspective view of the first component shown in FIG. 6A.
Figure 6C:
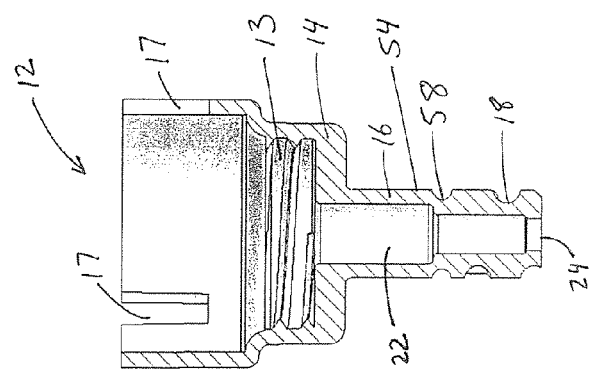
FIG. 6C is a cross-sectional view of the first component shown in FIG. 6A taken along E-E of FIG. 6A.
Figure 6B:
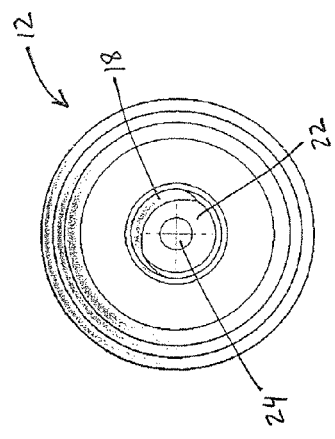
FIG. 6B is an end view of the first component shown in FIG. 6A taken from the nozzle end.
Figure 6A:
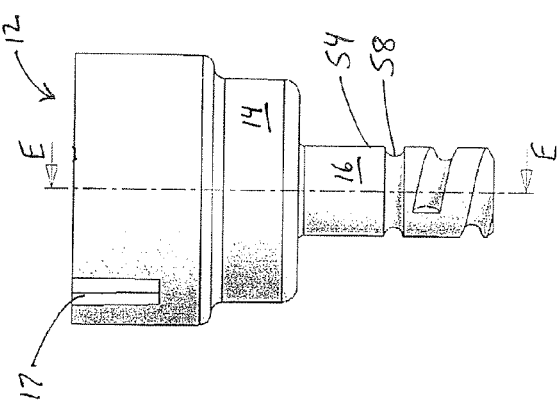
FIG. 6A depicts an embodiment of the first component of a device according to the invention.
Figure 7B:
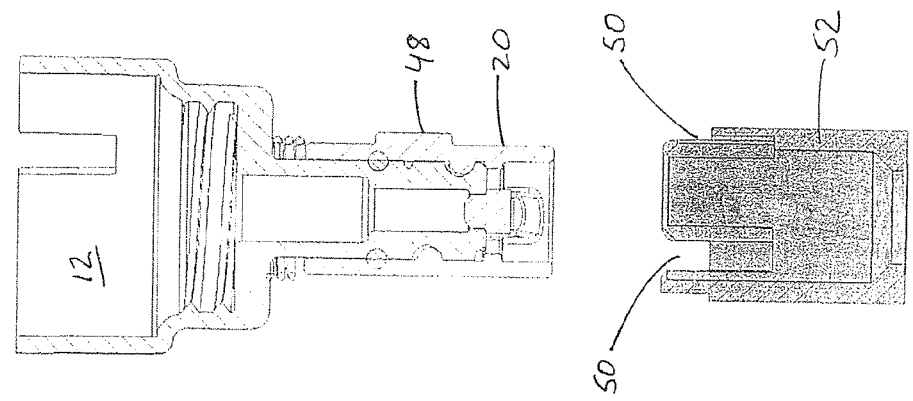
FIG. 7B is a cross-sectional view of the device and vaporizer receiving port of FIG. 7A taken along F-F in FIG. 7A.
Figure 7A:
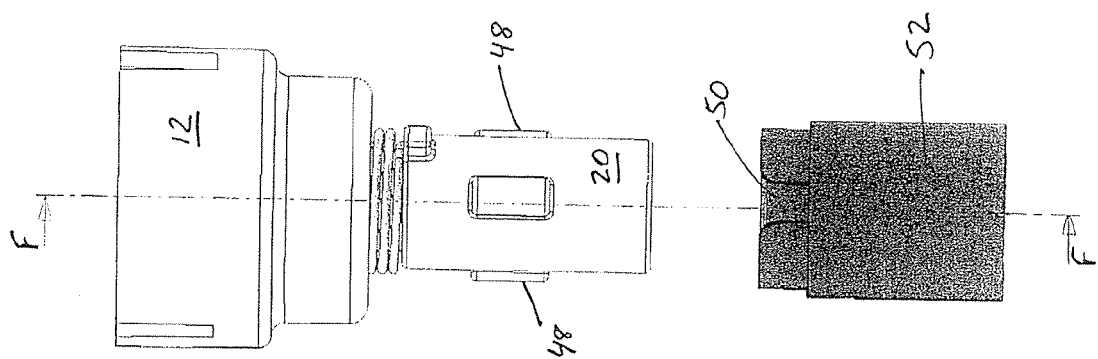
FIG. 7A depicts a device according to the invention in a "closed" position and a vaporizer receiving port.
Figure 8B:
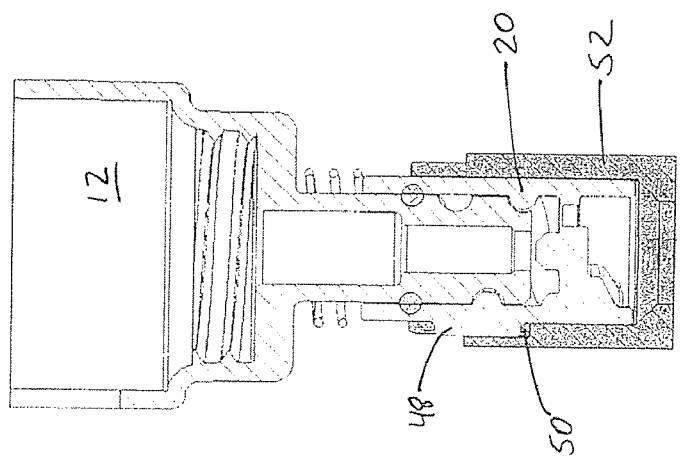
FIG. 8B is a cross-sectional view of the device and vaporizer receiving port of FIG. 8A taken along G-G in FIG. 8A.
Figure 8A:
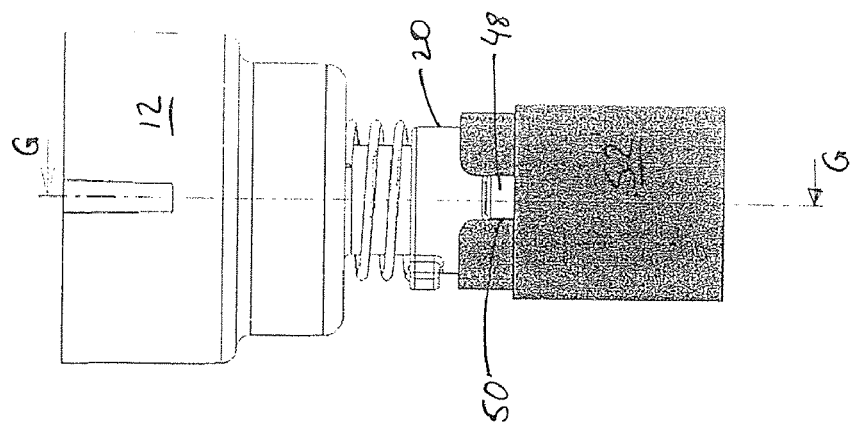
FIG. 8A depicts the device of FIG. 7A in an "open" position and inserted into the vaporizer receiving port.

An O-ring 56 may be disposed in a circumferential groove 58 of the first component 12, for example, as shown in FIGS. 2A and 6A. The O-ring 56 may protrude above an outer surface 54 of the first component so as to provide a fluid seal between the first component 12 and the second component 20.

The second component 20 may have an outer surface 46 which may be adapted for insertion into a vaporizer. The outer surface 46 may have a smooth cylindrical shape (see, e.g., FIGS. 5C and 5D). One or more indexing tabs 48 may be disposed on the outer surface 46. When more than one indexing tab 48 is used, the indexing tabs 48 may be evenly or unevenly spaced around a circumference of the second component 20. When the second component 20 is inserted into a vaporizer receiving port 52 of a vaporizer, the indexing tabs 48 may fit into keyways 50 of the vaporizer receiving port 52 (see, e.g., FIGS. 7A, 7B, 8A, and 8b). The indexing tab(s) 48 and keyway(s) 50 may prevent the second component from rotating relative to the vaporizer receiving port 52 such that the device 10 may be opened or closed by rotating the reservoir 70. A particular configuration of the keyways 50 may be used with a particular anesthetic. When the second component 20 has indexing tabs 48 that coincide with the keyways 50, the proper second component 20 for that vaporizer will be used.

The support member 34 of the second component 20 may have a downstream side 35 adapted for pushing a plunger 53 which may protrude into the vaporizer receiving port 52. The plunger 53 may operate an opening mechanism in the vaporizer which allows anesthetic liquid provided by the reservoir 70 through device 10 to enter the vaporizer. The downstream side 35 of the support member 34 may be, for example, substantially flat such that a force applied to the plunger 53 by the downstream side 35 is directed substantially along a longitudinal dimension of the plunger 53.

Figure 10D:
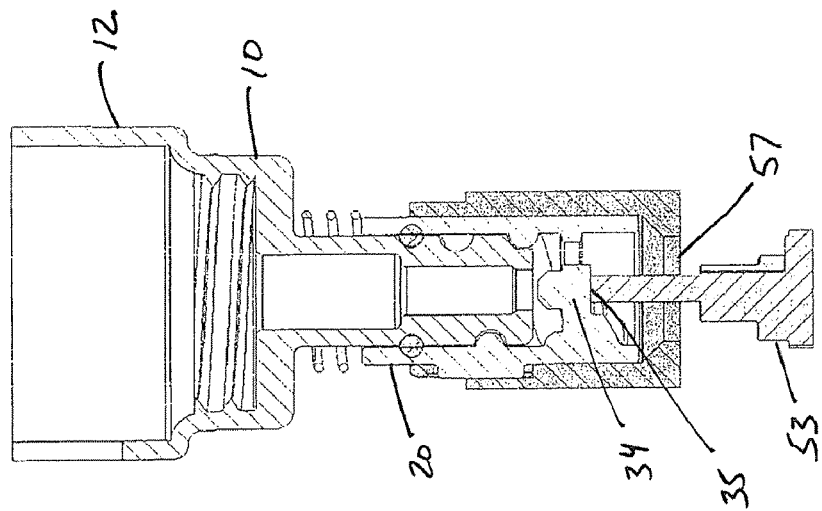
FIG. 10D is a cross-sectional view of the device and vaporizer receiving port of FIG. 10C taken along J-J in FIG. 10C.
Figure 10C:
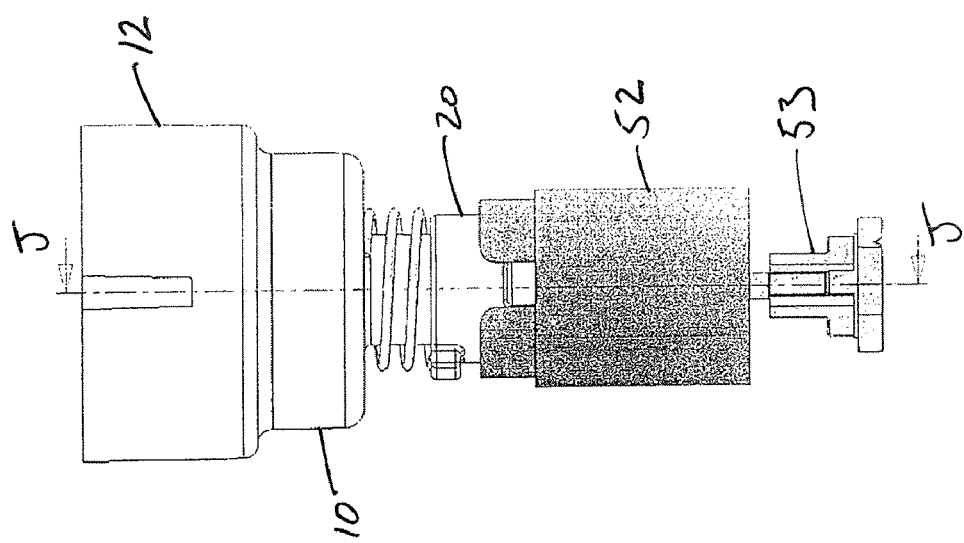
FIG. 10C depicts the device of FIG. 10A inserted into the vaporizer receiving port of FIG. 10A—both in "opened" positions.

FIGS. 10A and 10B depict a non-limiting example of a device 10 in a closed position (as described above) and a vaporizer receiving port 52 with a plunger 53. In this example, the vaporizer receiving port 52 is "closed" because the plunger 53 is configured to obstruct an outlet 57 of the vaporizer receiving port 52. FIGS. 10C and 10D depict the device 10 inserted into the vaporizer receiving port 52 and the downstream side of the support member has depressed the plunger 35, thereby removing the obstruction of outlet 57, and "opening" the vaporizer receiving port 52. In this manner, when a reservoir 70 with a device 10 is inserted into the vaporizer receiving port 52 of a vaporizer, the downstream side 35 of the support member 34 can depress the plunger 53 to open the vaporizer for anesthetic. The reservoir 70 may then be rotated so as to open the device 10 and allow liquid anesthetic to flow into the vaporizer.

Although the present invention has been described with respect to one or more particular embodiments, it will be understood that other embodiments of the present invention may be made without departing from the spirit and scope of the present invention. Hence, the present invention is deemed limited only by the appended claims and the reasonable interpretation thereof.

What is claimed is:

1. A device for controlling the flow of liquid anesthetic from an anesthetic reservoir comprising:
    a first component having a base and a nozzle, the base being configured so as to be capable of being sealed and affixed to an opening of a reservoir, the nozzle being externally threaded, and wherein a through hole extends through the base and the nozzle;
    a second component having:
        (a) an aperture defined by an inner surface of the second component and an outer surface which is cylindrically shaped for insertion into a vaporizer, and wherein the aperture has internal threads for engaging with the external threads of the nozzle;
        (b) a support member fixedly attached to the inner surface and extending into the aperture from the inner surface; and
        (c) a knob extending from the support member toward the internal threads,
    wherein the knob is configured to be capable of sealing the through-hole in the nozzle;
    wherein a fluid in the reservoir may exit the reservoir by way of the through-hole and the aperture when the knob does not seal the through-hole; and
    wherein twisting the first component and second component relative to each other causes the knob to seal or unseal the through-hole thereby preventing or allowing the flow of fluid.

2. The device of claim 1 further comprising a torsion spring attached to the first component and the second component and the torsion spring biasing the second component relative to the first component to cause the knob to seal the through hole.

3. The device of claim 2 wherein the second component further comprises a stud having a mounting hole for attaching the torsion spring.

4. The device of claim 1 further comprising one or more indexing tabs disposed on the outer surface of the second component.

5. The device of claim 4 wherein the indexing tabs are distributed around a circumference of the second component in a spaced apart relation according to a desired anesthetic.

6. The device of claim 1 wherein the base of the first component further comprises at least two notches capable of receiving at least one indexing nub on the reservoir.

7. The device of claim 1 wherein the first component further comprises a circumferential groove having an 0-ring disposed therein.

8. The device of claim 1 wherein a downstream side of the support member is capable of depressing a plunger.

9. The device of claim 1, wherein the support member has a first end fixedly attached to the inner surface and a second end extending into the aperture in cantilever fashion, the knob being attached to the second end.

10. The device of claim 1, wherein the first component has screw threads formed in the base, wherein the screw threads are adapted to mate with mating screw threads formed on an anesthetic reservoir.

* * * * *

UNITED STATES PATENT AND TRADEMARK OFFICE
CERTIFICATE OF CORRECTION

| | | |
|---|---|---|
| PATENT NO. | : 8,353,468 B2 | Page 1 of 1 |
| APPLICATION NO. | : 12/274819 | |
| DATED | : January 15, 2013 | |
| INVENTOR(S) | : Cuzydlo | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 758 days.

Signed and Sealed this
Twenty-seventh Day of August, 2013

Teresa Stanek Rea
*Acting Director of the United States Patent and Trademark Office*